United States Patent [19]

Böcker et al.

[11] Patent Number: 5,507,288
[45] Date of Patent: Apr. 16, 1996

[54] ANALYTICAL SYSTEM FOR MONITORING A SUBSTANCE TO BE ANALYZED IN PATIENT-BLOOD

[75] Inventors: Dirk Böcker, Heidelberg; Hans-Peter Haar, Wiesloch; Peter Blasberg, Weinheim; Reinhard Kotulla, Lambsheim, all of Germany

[73] Assignee: Boehringer Mannheim GmbH, Mannheim, Germany

[21] Appl. No.: 434,296

[22] Filed: May 3, 1995

[30] Foreign Application Priority Data

May 5, 1994 [DE] Germany .......................... 44 15 896.3

[51] Int. Cl.⁶ .................................................. A61B 5/00
[52] U.S. Cl. ........................ 128/633; 128/636; 128/637; 128/903
[58] Field of Search ................................. 128/632, 633, 128/635, 636, 637, 903

[56] References Cited

U.S. PATENT DOCUMENTS

| | | | |
|---|---|---|---|
| 4,637,403 | 1/1987 | Garcia et al. | 128/637 |
| 4,890,621 | 1/1990 | Hakky | 128/637 |
| 4,935,875 | 6/1990 | Shah et al. . | |
| 5,140,985 | 8/1992 | Schroeder et al. | 128/632 |
| 5,190,041 | 3/1993 | Palti | 128/635 |
| 5,400,794 | 3/1995 | Gorman | 128/903 |
| 5,417,222 | 5/1995 | Dempsey et al. | 128/696 |

FOREIGN PATENT DOCUMENTS

| | | |
|---|---|---|
| 3024824A1 | 1/1981 | Germany . |
| 3108767C2 | 11/1982 | Germany . |
| 3118740C2 | 10/1983 | Germany . |
| 3428630A1 | 2/1985 | Germany . |
| 3435647A1 | 7/1985 | Germany . |
| 3318746C2 | 8/1985 | Germany . |
| 3810008C1 | 10/1989 | Germany . |
| 4026426A1 | 2/1992 | Germany . |

(List continued on next page.)

OTHER PUBLICATIONS

IEEE Transactions on Biomedical Engineering, "New Non-invasive Transcutaneous Approach to Blood Glucose Monitoring: Successful Glucose Monitoring on Human 75 g OGTT with Novel Sampling Chamber", vol. 38, No. 8, Aug. 1991, pp. 752–757.

Primary Examiner—Angela D. Sykes
Assistant Examiner—Bryan Yarnell
Attorney, Agent, or Firm—Nikaido, Marmelstein, Murray & Oram

[57] ABSTRACT

Analytical system for monitoring patient blood concentration of a substance to be analyzed, comprising analysis-elements (12) containing reagents and an evaluation instrument comprising a measurement device to measure a change resulting from a reaction of the analyte with the reagents in order to determine, from the measurement values so obtained, analytical data representing element analysis data $C_A$.

In order to allow continuous monitoring of the analyte with good accuracy and a reduced number of invasive sample generation steps it is proposed that the analytical system further comprises (i) a sensor unit (2) portable on the patient body, said sensor unit (2) including a sensor (7) borne on the patient body for the direct and reagent-free measurement of a parameter correlating with the concentration of the analyzed substance and a transmitter for the wireless transmission of data signals; and (ii) a sensor-analysis means to ascertain sensor-analysis data $C_S$ from the measurement values of said parameter measured by said sensor; and the evaluation instrument further comprises a receiver to receive in wireless manner the data signals from the sensor unit (2), calibration means to calibrate the sensor-analysis data $C_S$ on the basis of the element-analysis data $C_A$ and (iii) a data memory for the long-term storage of analytical data, whereby said evaluation instrument forms a central unit (3) of an integrated analysis-element/sensor monitoring system (1).

20 Claims, 4 Drawing Sheets

FOREIGN PATENT DOCUMENTS

| | | |
|---|---|---|
| 4138702A1 | 9/1992 | Germany . |
| 4114448A1 | 11/1992 | Germany . |
| 4130369A1 | 3/1993 | Germany . |
| 4212498A1 | 10/1993 | Germany . |
| 4312093A1 | 10/1993 | Germany . |
| 4214263A1 | 11/1993 | Germany . |
| 4221848A1 | 1/1994 | Germany . |
| 4300499A1 | 7/1994 | Germany . |
| WO90/13872 | 11/1990 | WIPO . |

5,507,288

ANALYTICAL SYSTEM FOR MONITORING A SUBSTANCE TO BE ANALYZED IN PATIENT-BLOOD

BACKGROUND OF THE INVENTION

The invention concerns an analytical system for monitoring a substance to be analyzed (analyte) which is present in the blood of a patient.

The concentration of analytes in blood in many cases must be monitored regularly. This is especially the case when regular drug treatment is required in relation to the concentration of the particular substance. The most important example is diabetes-mellitus. Patients with this disease should constantly monitor their blood-sugar level to match their insulin injections to their need at the time and thereby to keep their blood-sugar levels (that is, the glucose concentration in blood) within specified limits. Exceeding such limits upward (hyperglycemia) or dropping below them (hypoglycemia) should be avoided with as much reliability as possible to prevent both critical acute conditions and grave long-term disabilities (for instance loss of eyesight).

The present invention in particular relates to monitoring the blood-glucose concentration though it is also applicable to other substances requiring analysis. No limitation on the general applicability of the invention is to be construed from any discussion hereafter relating to glucose determination.

Conventional analytical systems for monitoring blood-glucose concentration are composed of solid-state analysis-elements also called test carriers and an evaluation instrument. As a rule the analysis-elements and the evaluation instrument are specifically mutually matched and are provided as one system from the same manufacturer.

The analysis-elements contain reagents. When the elements are brought into contact with the test sample, the reaction between the analyte in the sample and the reagents causes a physically measurable change correlated to the concentration of said substance, in the analysis element. The evaluation instrument contains a measurement system measuring the said change and electronics to determine the concentration of the analyte on the basis of the measurement value obtained when measuring said change. Modern devices make use of microprocessors for the evaluating electronics, making possible software-controlled digital processing of the measurement values into signals corresponding to the concentration of the substance being analyzed. As a rule these analytical data are displayed in units of concentration on an alphanumeric display. However the expression "analytical data" in the sense of the invention also covers electrical signals representing the analytical results in other ways, for instance as signals to control offset displays of information relating to the concentration of the analyte such as "ideal range", "upper standard range", "upper danger zone", etc.

Different kinds of analysis-elements are known that involve different physico-chemical principles regarding the principles of reaction and the measurable change correlated to concentration. Conventional analysis systems are foremost photometric or electrochemical.

As regards photometric analytical systems, the analysis-elements contain a system of reagents. The reaction thereof with the analyte causes a photometrically detectable change (color change). In general the reagents are present in a porous-plastic or paper matrix forming a test zone of the analyzing element, the color of said matrix changing as a function of concentration. This color change can be quantitatively determined using reflection photometry.

Electrochemical analysis-elements contain a system of electrochemical reagents. The reaction thereof with the analyte affects the electrical potential across two terminals of the analysis-elements and/or the current level between two terminals of the analyzing element when the voltage across said terminals is fixed. In this case therefore the changing physically measurable quantity is the voltage or the current and is determined by a corresponding voltage or current sensor integrated into the instrument. The change of said measurement value correlating to the concentration of the analyzed substance is converted, preferably again using microprocessor evaluation electronics, into analytical data (concentration of analyzed substance).

Analytical systems operating by means of reagent containing analysis-elements (hereinafter referred to as "element-analysis systems") have become highly accurate and are handled easily enough that the patient himself/herself may use them for constant monitoring of the blood-glucose concentration (home monitoring). However they entail the significant drawback that each particular analysis requires withdrawing a drop of blood which then is placed in contact with an analysis-element. As a rule this procedure is implemented by piercing the finger, in other words, each analysis entails painful skin injury with some danger of infection. Such a procedure is called "invasive analysis".

In order to allow continuous monitoring of the concentration of a substance to be analyzed in blood while providing good accuracy and a lesser number of invasive interventions to secure samples, the invention, based on an analytical system of the type discussed before, discloses a system which includes a sensor unit portable on the patient body and comprising a sensor which, free of reagents, directly measures at the patient body a parameter correlating with the concentration of the analyzed substance, said unit further comprising a transmitter to wirelessly transmit data signals. Said system furthermore includes sensor evaluation electronics to determine sensor-analysis data from the sensor measurement values of the measured parameter. The evaluation instrument is the central unit of an integrated analysis-element/sensor monitoring-system and includes a wireless receiver to receive the data signals from the sensor unit, further calibrating means to calibrate the sensor-analysis data on the basis of the analytical data from the analysis-element ("element analysis data") and a data memory for the long-term storage of analytical data.

Reagent-free, sensor-analysis systems for determining blood analytes have been described in various embodiments. For some substances to be analyzed (especially the blood oxygenation values and the blood gas concentrations) such systems have become practically significant. However for a number of other substances to be analyzed, in particular glucose, they have not been adequately practical.

A survey of non-invasive methods to determine glucose is given in "PHYSICOCHEMICAL DETERMINATION OF GLUCOSE IN VIVO" by J. D. Kruse-Jarres, J. Clin. Chem. Clin. Biochem. 26, 1988, pp 201–8.

Foremost the invention concerns systems employing the interaction between irradiated light and the tissue of a living human (preferably the dermal tissue) for the purpose of analytically determining the concentration of an analyte therein. It is assumed that the concentration of the analyte in the (blood-circulating) tissue correlates adequately for practical purposes with the corresponding concentration in the blood. In such systems the sensor unit includes a light emitter irradiating the tissue. Furthermore a light detector is present by means of which, following its interaction with the tissue, light leaving the body part is sensed in order to determine a measurable physical light property which changes by interaction with the tissue. In such methods, this measurable physical property forms a parameter which correlates with the concentration of the analyzed substance.

Most methods of this kind known so-far are based on spectroscopic analysis. The characteristic absorption (caused by the vibrational and rotational states of the molecules of the analyzed substance) is determined therein by ascertaining the dependence of optical absorption on the light wavelength. In practice typically light of different wavelengths from a narrow-band light emitter is irradiated and the light received by the light detector is then measured. Alternatively the irradiation may be from a broad-band light emitter and a wavelength-selective measurement may then be carried out at the detection side. The absorption bands of the molecules under discussion (in particular of glucose) are far into the infrared range of light. However, tissue water causing strong optical absorption in this range, most authors suggest measurement wavelengths in the near infrared, whereby harmonics of the molecular oscillatory and rotational states may be detected. Illustrative such systems are described in EP-A0 160 768, in WO 93/00856 and in U.S. Pat. No. 5,028,787.

In an especially preferred embodiment of the invention, a sensor system is used wherein a light parameter is determined that depends on the tissue's index of refraction. This method is substantially based on the finding that the change in index of refraction of the liquid in the tissue relating to the glucose concentration may be used as the parameter correlated to the glucose concentration.

For the implementation of this method a measurement-technique has been suggested in which signals are determined which are affected by the multi-scattering of light by scattering centers in the tissue. Such a procedure is described in the international patent application PCT/DE 93/01058. Under the conditions of measurement described in said publication, multi-scattering causes enhancement of the effect tied to the change in index of refraction, and said enhancement can be ascertained as a comparatively strong and hence well measurable signal change. The cited reference contains further details which are incorporated by reference into the present disclosure.

German patent application 43 37 570 describes analysis of glucose based on the determination of a light parameter corresponding to the light transit time in the tissue. Such a transit time parameter may be directly the time of travel of an exceedingly short light pulse. However it is much simpler to ascertain instead the phaseshift of light within the tissue as a transit-time parameter which correlates with the tissue glucose concentration.

Lastly the simultaneously filed German patent application 44 15 728 "METHOD AND DEVICE FOR ANALYZING GLUCOSE IN A BIOLOGICAL SAMPLE" describes how to determine changes in tissue index-of-refraction using low-coherence interferometry. Such determination may take place directly by ascertaining the light's optical path in the tissue or indirectly in such manner that the light scattering coefficient in the tissue is being ascertained. The scattering coefficient is affected decisively by the relation between the index of refraction of the liquid and that of the tissue scattering centers (for instance cells). Again the contents of said application is incorporated by reference into the present disclosure.

SUMMARY OF THE INVENTION

In the invention, such a non-invasive sensor-analysis-system is combined with an invasive analytical system operating with a reagent-based analyzing element. The sensor-analysis-system is composed of a movable, battery-operated sensor unit worn on the patient-body and of an evaluating device which is stationary in the sense that it is not borne on the patient-body but is situated at an appropriate location, for instance in the dwelling of the patient. Preferably however the central unit is small and lightweight enough to be easily carried along by the patient if or when leaving said dwelling for some time (for instance for several days). The base unit and the central unit are linked by wireless data transmission. Said link may be implemented in a variety of ways, for instance using IR light, high frequency radio waves or ultrasonics.

The sensor unit borne on the patient-body and the stationary central unit jointly assume the functions of the sensor-analysis-system. The system functions can be assigned to the two units in different ways. Basically a sensor unit may be designed without intelligence of its own, its function being merely to determine the sensor measurement values and to transmit these in wireless manner to the central unit. Preferably however the sensor unit is designed with its own intelligence, that is, it comprises a microprocessor data-processing system as evaluation means in order to ascertain sensor analysis data from the measurement values of the at least one sensor of the sensor unit that correspond to the concentration of the substance being analyzed. As a result it is possible to provide the sensor unit with its own display for indicating the concentration data of the analyzed substance, illustratively merely issuing an acoustic or optic warning when specified limits of the glucose concentration are crossed upward or downward. Advantageously furthermore in such embodiment the link between the sensor unit and the central unit is interactive, that is, not only are analytical data from the analyzing element transmitted from the sensor unit to the central unit, but vice-versa data from the central unit are also made available to the sensor unit. This feature may apply in particular to calibration required by the sensor unit to determine the concentration of the analyzed substance.

It is furthermore significant in the present invention that the central unit of the sensor-analysis-system be simultaneously the evaluation instrument of the invasive element-analysis system and that it serves for calibrating the sensor-analysis sub-system on the basis of the test data of the element-analysis sub-system.

Compared with heretofore conventionally used analytical systems, a primary advantage of the analytical system of the invention is that current analytical data are continuously present in real time and that reliable information about the rate of change of the glucose concentration is available any time. This is especially important for groups at risk among the diabetics, for instance diabetics tending toward hypo- or hyper-glycemia during night rest. Furthermore permanent monitoring of glucose values is especially important during times of increased body exertion, for instance sports activities. For diabetics on insulin therapy it is especially important to be provided with the feasibility of determining the instantaneous trend of the glucose value (rising or falling) qualitatively and quantitatively in order to determine the required quantity of insulin.

The invention is elucidated below by means of embodiments illustratively shown in the FIGURES.

DETAILED DESCRIPTION OF THE PREFERRED EMBODIMENTS

Figure 1:
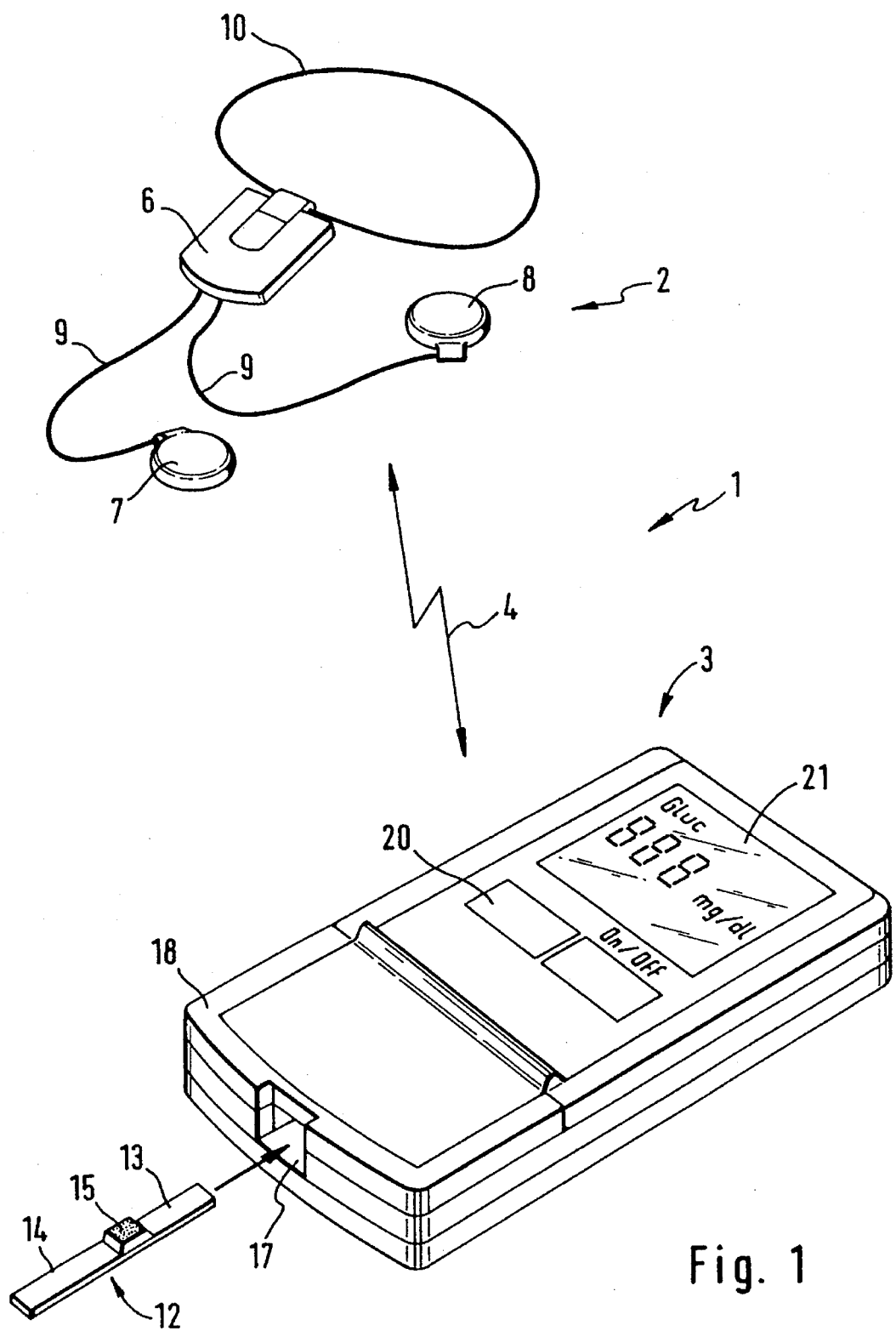
FIG. 1 is a perspective view of the components of an analytical system according to the invention.

The integrated analysis-element/sensor system IASS 1 shown in FIG. 1 is composed of a sensor unit 2 borne on the body of the patient and of a central unit 3 linked with the sensor unit 2 by wireless data transmission symbolized by the arrow 4. In the shown preferred embodiment, the sensor unit 2 is composed of the base unit 6 and of two sensors 7, 8 connected by cables 9 to the base unit 6. The base unit 6 may be worn by a neck strap 10 around the neck of the patient. Obviously it may be affixed also in some other way, for instance by a shoulder strap or a belt clip to the patient body.

In principle, operation may be with only one sensor. However two or more sensors may be advantageous in order to allow measuring of a parameter correlating with the glucose concentration at several body test sites simultaneously, with an increase in accuracy being provided for instance by averaging the measurement values or by selecting the better test values by means of predetermined reliability criteria.

The central unit 3 comprises the typical features of an evaluation instrument commonly used in element-analysis-systems. In the case shown, it serves to evaluate an analysis-element 12 in the form of a glucose test strip 13 with a base layer 14 and a test zone 15. For evaluation, the analysis-element 12 is inserted into a test duct 17 located beneath a flap 18 of the device 3. A keypad 20 is provided to operate the central unit 3. A display 21 serves as information output, in particular to display analytical data.

The evaluation means for evaluating the analysis-element, which is integrated into the central unit 3, is of conventional design and therefore need not be described in further detail. Relevant information is offered in numerous publications. Illustratively the general instrument design is described in European patent application 0 492 326 and applicable measurement electronics is described in the European patent application 0 075 767.

Figure 2:
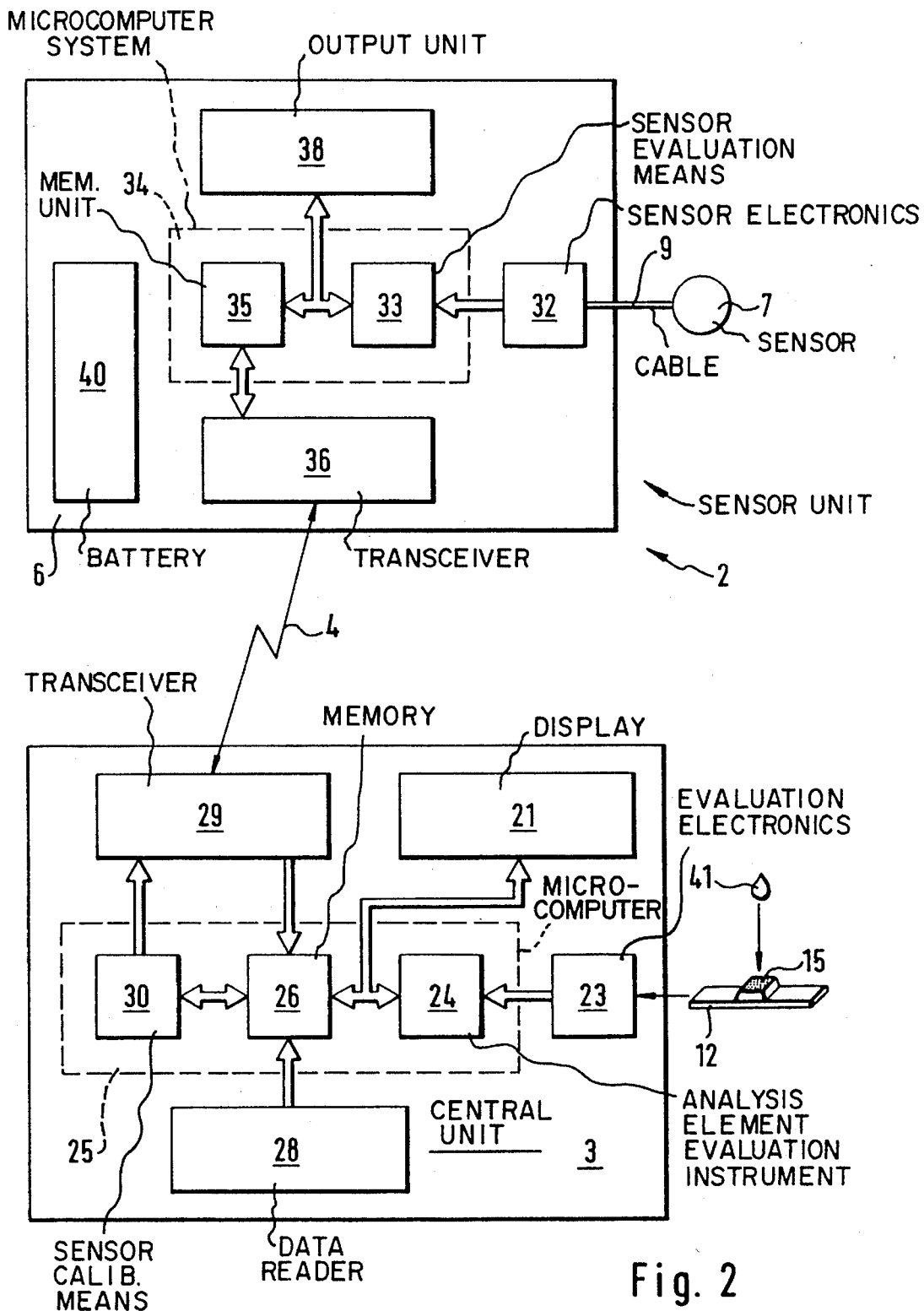
FIG. 2 is a functional block diagram.

FIG. 2 is a block diagram of the essential functional components of the central unit 3 and of the sensor unit 2.

The central unit 3 contains a measurement device 23 to measure a change in the analysis-element 12 correlating with the change of the concentration of the analyzed substance, for instance a reflection photometer, allowing to measure a change of the color of the test zone 15. The measurement device 23 generates electrical signals corresponding to the measurement value R of the change correlating with the concentration.

The measurement values R are fed to evaluation electronics 24 which is a part of the a micro-computer 25 which also includes a data memory 26. By means of an evaluation curve stored in the data memory 26 which describes the functional relationship of the sought concentration C and the test value R, namely $C_A=f(R)$, the evaluation electronics 24 computes the sought concentration C of the analyzed substance and feeds these element-analysis data $C_A$ to the memory 26 where they are stored. The analysis data $C_A$ are displayed automatically or by means of a special command in the display 21.

The evaluation curve $C_A=f(R)$ may be permanently stored in the central unit 3. Preferably however a separate, batch-specific evaluation curve shall be used for each new manufactured batch of analysis-elements 12 and shall be transmitted to the central unit by means of a suitable data medium in machine-readable form. For that purpose the central unit comprises a data reader 28, illustratively a bar-code reader, to read a bar code affixed to the analysis-element itself or to an additional code carrier. The bar code is included in each pack of analysis-elements and contains the batch-specific evaluation curve. Further details are provided in the European patent application 0 492 326.

Figure 3:
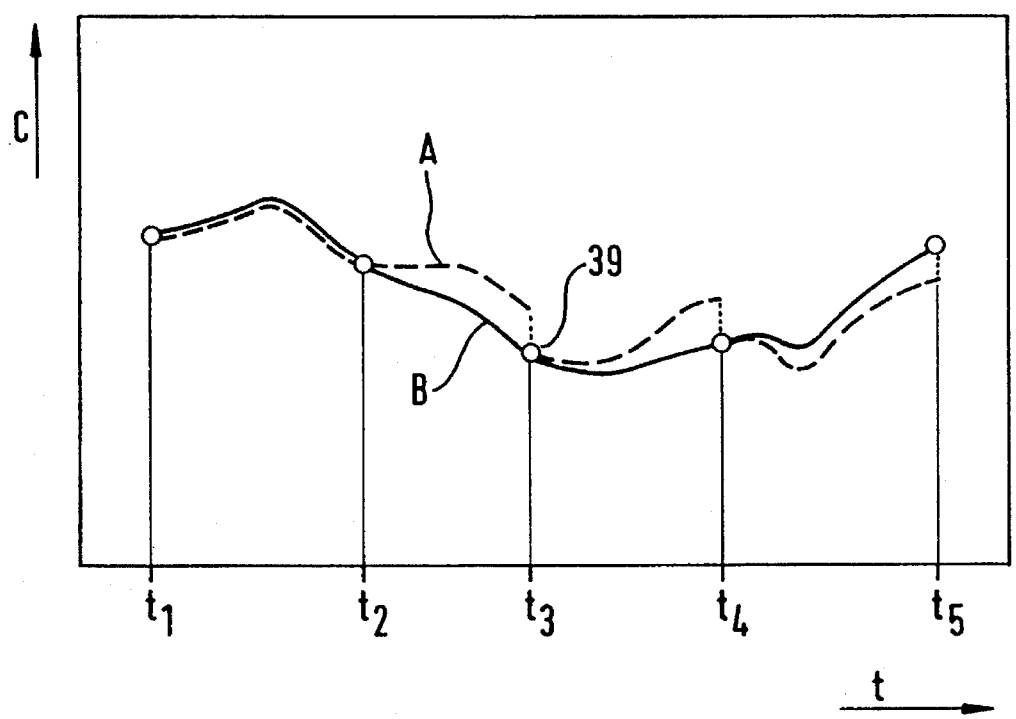
FIG. 3 is a plot of the analytical data as a function of time, explaining a calibration procedure.

In addition to the above described functional components which are conventional in analysis-element evaluation instruments, the central unit 3 furthermore comprises a transceiver 29 for wireless transmission of data, and a sensor calibration means 30 which in practice preferably is implemented as software and therefore is shown in FIG. 3 as being part of the microcomputer 25. These components link the analysis-element sub-system to the sensor sub-system in the manner further elucidated below.

The base unit 6 of the sensor unit 2 contains sensor operation device 32 connected to at least one sensor 7. This sensor operation device 32 contains the elements required to operate the sensor 7 and thereby to measure at the patient body a parameter correlating with the glucose concentration. The preferred embodiment includes light irradiating means which may be LEDs mounted in the sensor 7 itself and powered through the cable 9. Alternatively one or more light sources may be present in the base unit 6, the cable 9 containing optic fibers transmitting the light into the sensor 7. Correspondingly semiconducting light detectors are present in the sensor 7 and/or the base unit 6 to detect the light after its interaction with the patient tissue. The sensor operation device 32 furthermore contains electronic components such as amplifiers to process the received signal into a sensor measurement value S correlating with the concentration of the analyzed substance. The sensor measurement value S is fed to sensor evaluation electronics or means 33 preferably in the form of components of a micro-computer system 34 which also includes a memory unit and which is integrated into the base unit 6. In practice and like the analysis-element evaluation instrument 24, the sensor evaluation-electronics device 33 computes analytical data (concentrations) C, by means of an evaluation curve $C_S=g(S)$ stored in the memory unit 35, from the measurement values S, said calculation being in practice software controlled. The evaluation curve $C_S=g(S)$ is transmitted in wireless manner from the central unit 3 to the base unit 6. For that purpose the base unit 6 is fitted with a transceiver 36 making possible in cooperation with the transceiver 29 of the central unit wireless transmission of data between the two units 3, 6.

The computed concentration data (sensor analysis data $C_S$) are stored in the memory unit 35. They may be output independently of the central unit 3 by an output unit 38, the design of the output unit 38 in the base unit 6 is chosen for minimum size and consumption of battery power. Its main purpose is to issue an alarm in case critical limit values of the glucose concentration are crossed in the dangerous direction. Appropriately the output unit 38 may be embodied as an LED display with three LEDs (normal range, danger of excess sugar, danger of sugar deficiency). Alternatively or in addition, an acoustic signal may be provided.

FIG. 2 shows the power-supply battery 40 being part of the base unit 6. This is important since the power drain of analytic sensors is comparatively high. Therefore the battery 40 should be rechargeable and a voltage monitor (not shown) is integrated into the base unit 6 to alert in timely manner to the need for battery exchange.

When using the analytical system of the invention, the patient fitted with the sensor unit 2 may be away for a substantial time from the stationary central unit 3 without running into problems. During this time the sensor-analysis data $C_S$ are stored in the memory 35. Upon returning home, and when the patient is sufficiently close to the central unit 3 to allow wireless exchange of data between the units 3 and 6, the sensor-analysis data $C_S$ which were acquired in the meantime are transferred from the memory 35 into the memory 26 of the central unit. The patient is able any time to make a calibration using an analysis-element 12. Appropriately the central unit 3 comprises time-keeping device reminding the patient frequently enough to carry out an analysis by means of an analysis-element for purposes of calibration. Each time such an analysis is performed, a new evaluation curve $C_S=g(S)$ is determined in the central unit 3 and transmitted to the sensor unit 2. The cooperation of the units 3 and 6 during calibration of the overall system is discussed further below.

As already described, the element-analysis data $C_A$ are calibrated by means of the evaluation curve $C_A=f(R)$ which is preferably entered in the form of a machine-readable code through the data reader 28 into the memory 26. Accordingly the analytical data $C_A$ generated by means of the analysis-elements will be satisfactorily accurate. A $C_A$ value becomes available when the patient stabs his/her finger to obtain a drop of blood 41 which then is analyzed by means of the analysis-element 12 and the measurement device 23 and evaluation electronics 24, 24. Such a measurement may take place at substantial time intervals, for instance once or twice daily. FIG. 3 shows the analysis data determined at times $t_1$ through $t_5$ in the form of data points 39.

By means of its sensor operation device 32 and evaluation electronics 33, the sensor 7 generates sensor-analysis data $C_S$, said generation taking place continuously or at such minute intervals that a practically continuous sequence of $C_S$ values is stored in the memory 35 and can be transferred to the central unit 3 when the units 2 and 3 are in the mutual data transmission mode. FIG. 3 shows the time-function of the $C_S$ values as the dashed line A. Element-analysis data $C_A$ are used to calibrate the sensor-analysis data $C_S$. This procedure may be carried out for instance in such a way that at each calibration time $t_1$ through $t_5$ the sensor calibration means 30 compares the analytical data $C_A$ and $C_S$ stored in the memory 26. The sensor calibration means 30 determines from said comparison a new corrected evaluation curve $C_S=g(S)$ which it then transfers through the transceiver components 29, 36 to the base unit 6 where the new evaluation curve will be used in the memory 35 for future computations of sensor-analysis data $C_S$ using the sensor evaluation electronics 33. The new evaluation curve $C_S=g(S)$ ascertained during calibration may be used simultaneously to back-correct sensor-analysis data already stored in the memory 26 at least as far back as the time of the preceding element-analysis. Accordingly as regards the example shown in FIG. 3, a backward correction to the time $t_1$ may be achieved on the basis of the concentration value $C_A(t_2)$ obtained at time $t_2$. Similar considerations apply to going back from the time $t_3$ to the time $t_2$ etc. The corrected function of the sensor-analysis data following calibration is shown by the solid line B in FIG. 3.

This calibration method was described as an example only. Obviously it may be implemented in a different way, in particular when adapted to specific evaluation methods used for determining the analytical data $C_S$ or $C_A$. Numerical mathematical procedures for determining one concentration value $C_S$ from a large number of test values (for instance intensity values at many different wavelengths) are especially applicable. Among these procedures is the partial least-squares method.

The storage capacity of the memories 35 and 26 in the sensor and central units 2 and 3 respectively is made to match the particular applications. The memory 35 is used merely for the intermediate storage of relatively small volumes of data, namely the concentration values for the maximum time interval during which the patient together with his/her sensor unit 2 is away from the central unit 3. Preferably the capacity of the memory 35 is adequate for the amount of data generated in a time interval of at least 2 h, preferably at least 8 h. As a rule the memory 26 of the central unit 3 is substantially larger and may store both analytical and calibration data generated over long time intervals (at least one week). Appropriately the central unit 3 is fitted with an interface (not shown) whereby said data are transferred as required for further processing for instance to a PC used in the medical office to store the patient data.

The display of the analytical data by the central unit 3 may be alpha-numeric as shown in FIG. 1. Preferably the display 21 of the central unit 3 is graphic and allows a graphical representation of the time-sequence of the sensor-analysis data. In the display shown in FIG. 4, for instance, the instantaneous glucose value is symbolized by the central black strip 50. The light-gray display zone 51 corresponds to the standard range of the glucose values, whereas the dark-gray zone 52 shows the upper alarm zone (danger of hyperglycemia) and the lower black zone is the lower alarm range (danger of hypoglycemia). The trend at the time, in this case rising glucose values, is indicated by an arrow 54 in the display.

Figure 5:
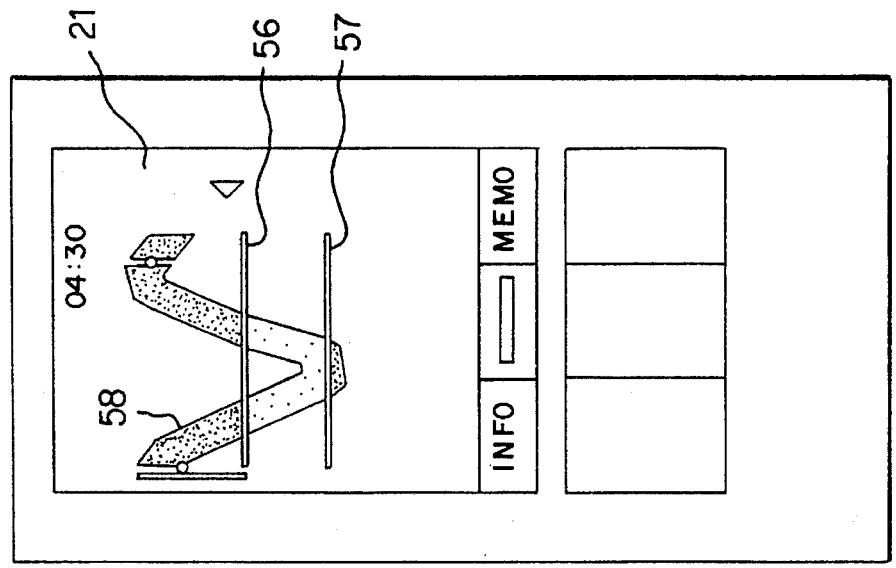
FIG. 5 is a top view of a central unit with a second embodiment of a graphics display.

The time function of the glucose values is shown over a more substantial time interval in the graph display of FIG. 5. The standard range of the glucose values is indicated by two warning limits 56, 57 at the middle of the display. The sequence of the glucose values is shown as a comparatively broad line 58. Already for some time this line 58 has been in the upper alarm zone of FIG. 5 and, for instance following an injection of insulin, now begins to drop.

Figure 4:
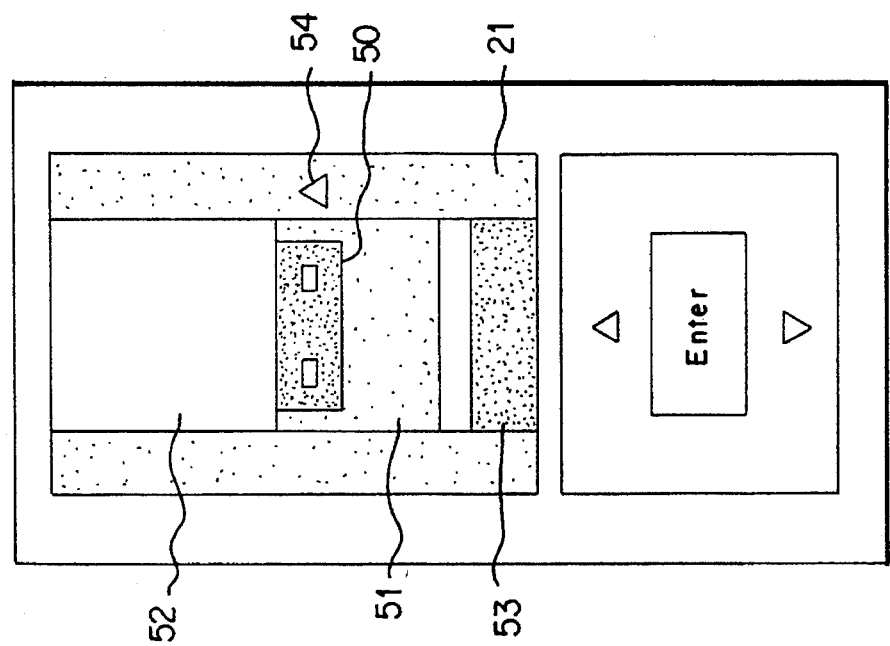
FIG. 4 is a top view of a central unit with a first embodiment of a graphics display.

The graph displays of FIGS. 4 and 5 make use of the special ability of the system of the invention to reliably and practically continuously determine the glucose values. The evaluation means 24 of the central unit 3 (where called for also the evaluation means 33 of the base unit 6) for that purpose again contains a preferably software driven discriminator permitting the determination of the glucose-value sequences at any time and hence the trend. This additional information is highly valuable in the therapy of diabetes mellitus.

We claim:

1. An analytical system for monitoring and analyzing a concentration of a substance in a blood sample of a patient, said system comprising:

at least one analysis element containing a reagent thereupon, said reagent for reacting with the substance in the blood when said at least one analysis element has been brought in contact with the sample, thereby causing a measurable change in the analysis element which correlates with the concentration of the substance;

an evaluation instrument having a measuring device therein, said measuring device for measuring the measurable change in the analysis element, the evaluation instrument also including an evaluation means for determining sample-analysis data from the measured change; said analytical system further comprising a portable sensor unit configured to be carried on the patient, said portable sensor unit including a first sensor means for non-invasive determination of a measured value of a parameter correlating with the concentration of the substance in the blood of the patient, said portable sensor unit also including a transmitter means for wireless transmission of data signals representing the non-invasively measured parameter; and sensor analysis means for ascertaining sensor-analysis data from the measured values of the parameter by the first sensor means;

said evaluation instrument further comprising a receiver means for wirelessly receiving the data signals from the sensor unit, calibration means for calibrating the sensor-analysis data based upon the sample-analysis data, and a data memory means coupled to said calibration means for storing data therein.

2. An analytical system as recited in claim 1, wherein the portable sensor unit comprises a light source for irradiating light into living tissue of the patient, and a light detector for detecting light exiting the living tissue of the patient, after the light has interacted with the tissue, thereby providing data indicative of a physical light property which varies based upon an interaction of the light with the tissue, thereby resulting in the parameter which correlates with the concentration of the analyzed substance in the patient blood, and wherein the sensor analysis data is ascertained from the parameter.

3. An analytical system as recited in claim 1, wherein said portable sensor unit comprises a base unit and the first sensor means, said base unit and said first sensor means being operably connected by cables, said base unit including a power supply for the first sensor means.

4. An analytical system as recited in claim 3, wherein the portable sensor unit further comprises a second sensor means, said second sensor means being connected by a cable to the base unit, wherein said first and second sensor means provide first and second measured values for correlation with the concentration of the analyzed substance in the patient blood.

5. An analytical system as recited in claim 1, wherein the sensor analysis means is provided in said portable sensor unit.

6. An analytical system as recited in claim 5, wherein the portable sensor unit also comprises display means for displaying information representing the sensor analysis data.

7. An analytical system as recited in claim 5, wherein the transmitter means of the portable sensor unit and the receiver means of the evaluation instrument are configured to form a transceiver system, said transceiver system conducting an interactive data exchange between the sensor unit and the evaluation instrument.

8. An analytical system as recited in claim 1, wherein said sensor unit includes a storage means for storing the sensor analysis data.

9. An analytical system as recited in claim 8, wherein said storage means stores the sensor analysis data for a time interval of at least eight hours.

10. An analytical system as recited in claim 9, wherein said storage means stores the sensor analysis data for a time interval of at least two hours.

11. An analytical system as recited in claim 1, wherein the evaluation instrument comprises a graphical display, said graphical display being configured to graphically represent the sensor analysis data over a period of time.

12. An analytical system as recited in claim 11, wherein said graphical display can be varied to provide a plurality of display modes for displaying variational trends of the sensor analysis data.

13. An analytical system as recited in claim 4, wherein said sensor analysis means ascertains the sensor-analysis data from the first and second measured values by averaging said first and second measured values.

14. An analytical system as recited in claim 4, wherein said sensor analysis means ascertains the sensor-analysis data from the first and second measured values by selecting one of the first and second measured values.

15. A method for monitoring and analyzing a concentration of a substance in a blood sample of a patient, comprising the steps of:

applying the blood sample to an analysis element having a reagent thereupon, wherein said reagent reacts with the substance in the blood sample, thereby causing a measurable change in the analysis element correlating with the concentration of the substance;

measuring the measurable change in the analysis element;

inputting measurement values of said measurable change into an evaluation instrument for determining sample-analysis data based upon the measured change;

non-invasively measuring a parameter correlating with the concentration of the substance in the blood of the patient with a portable sensor unit, said step of non-invasively measuring including the steps of irradiating light into living tissue of the patient, and detecting light exiting the living tissue, thereby providing data indicative of a physical light property which varies based upon an interaction of the light with the tissue;

wirelessly transmitting data signals representing the non-invasively measured value to a receiver which is a part of the evaluation instrument;

receiving said wirelessly transmitted data signals in the receiver;

determining sensor-analysis data from the transmitted data signals, said sensor-analysis data representing the concentration of the substance in the blood of the patient.

16. A method as recited in claim 15, further comprising a step of storing the sensor-analysis data in a memory.

17. A method according to claim 15, wherein said step of determining includes a step of correcting the sensor-analysis data by comparison with the sample-analysis data.

18. A method for monitoring and analyzing a concentration, of a substance in a blood sample of a patient, said method comprising the steps of:

providing an evaluation instrument for evaluating a concentration of a substance in a blood sample, said step of evaluating comprising the steps of applying the blood sample to an analysis element having a reagent thereupon, wherein said reagent reacts with the substance in the blood sample, thereby causing a measurable change in the analysis element correlating with the concentration of the substance, measuring the measurable change in the analysis element, determining sample-analysis data based upon the measured change, inputting the sample-analysis data to said evaluation instrument, thereby providing calibration information therefor; said method further comprising the steps of non-invasively measuring a parameter correlating with the concentration of the substance in the blood of the patient with a portable sensor unit, said step of non-invasively measuring including the steps of irradiating light into living tissue of the patient, and detecting light exiting the living tissue, thereby providing data indicative of a physical light property which varies based upon an interaction of the light with the tissue;

wirelessly transmitting data signals representing the non-invasively measured value to a receiver;

receiving said wirelessly transmitted data signals in the receiver;

determining sensor-analysis data from the transmitted data signals, said sensor-analysis data representing the concentration of the substance in the blood of the patient.

19. A method as recited in claim 18, further comprising a step of storing the sensor-analysis data in a memory.

20. A method according to claim 18, wherein said step of determining said sensor-analysis data includes a step of correcting the measured values based upon the sample-analysis data.

* * * * *

UNITED STATES PATENT AND TRADEMARK OFFICE
CERTIFICATE OF CORRECTION

PATENT NO.   : B1 5,507,288
DATED        : July 8, 1997
INVENTOR(S)  : Böcker et al.

It is certified that error appears in the above-identified patent and that said Letters Patent is hereby corrected as shown below:

Column 1,
Line 43, after "sensor-analysis" insert therefor -- system --.

Column 4,
Line 5, delete "iradiating" insert therefor -- irradiating --.

Signed and Sealed this

Eighteenth Day of March, 2003

JAMES E. ROGAN
*Director of the United States Patent and Trademark Office*

REEXAMINATION CERTIFICATE (3261th)

United States Patent [19]
Böcker et al.

[11] B1 5,507,288
[45] Certificate Issued Jul. 8, 1997

[54] ANALYTICAL SYSTEM FOR MONITORING A SUBSTANCE TO BE ANALYZED IN PATIENT-BLOOD

[75] Inventors: Dirk Böcker, Heidelberg; Hans-Peter Haar, Wiesloch; Peter Blasberg, Weinheim; Reinhard Kotulla, Lambsheim, all of Germany

[73] Assignee: Boehringer Mannheim GmbH, Mannheim, Germany

Reexamination Request:
No. 90/004,271, Jun. 7, 1996

Reexamination Certificate for:
Patent No.: 5,507,288
Issued: Apr. 16, 1996
Appl. No.: 434,296
Filed: May 3, 1995

[30] Foreign Application Priority Data

May 5, 1994 [DE] Germany .................. 44 15 896.3

[51] Int. Cl.$^6$ ........................................ A61B 5/00
[52] U.S. Cl. ........................ 128/633; 128/636; 128/637; 128/903
[58] Field of Search .................. 128/632, 633, 128/635–637, 903; 422/82.05

[56] References Cited

U.S. PATENT DOCUMENTS 4,140,963  2/1979  Rao et al. .
5,281,395  1/1994  Markart et al. ............... 422/82.05

FOREIGN PATENT DOCUMENTS

0492326A3  7/1992  European Pat. Off. .
WO92/00513  1/1992  WIPO .
WO92/22804  12/1992  WIPO .

*Primary Examiner*—Lee S. Cohen

[57] ABSTRACT

Analytical system for monitoring patient blood concentration of a substance to be analyzed, comprising analysis-elements (12) containing reagents and an evaluation instrument comprising a measurement device to measure a change resulting from a reaction of the analyte with the reagents in order to determine, from the measurement values so obtained, analytical data representing element analysis data $C_A$.

In order to allow continuous monitoring of the analyte with good accuracy and a reduced number of invasive sample generation steps it is proposed that the analytical system further comprises (i) a sensor unit (2) portable on the patient body, said sensor unit (2) including a sensor (7) borne on the patient body for the direct and reagent-free measurement of a parameter correlating with the concentration of the analyzed substance and a transmitter for the wireless transmission of data signals; and (ii) a sensor-analysis means to ascertain sensor-analysis data $C_S$ from the measurement values of said parameter measured by said sensor; and the evaluation instrument further comprises a receiver to receive in wireless manner the data signals from the sensor unit (2), calibration means to calibrate the sensor-analysis data $C_S$ on the basis of the element-analysis data $C_A$ and (iii) a data memory for the long-term storage of analytical data, whereby said evaluation instrument forms a central unit (3) of an integrated analysis-element/sensor monitoring system (1).

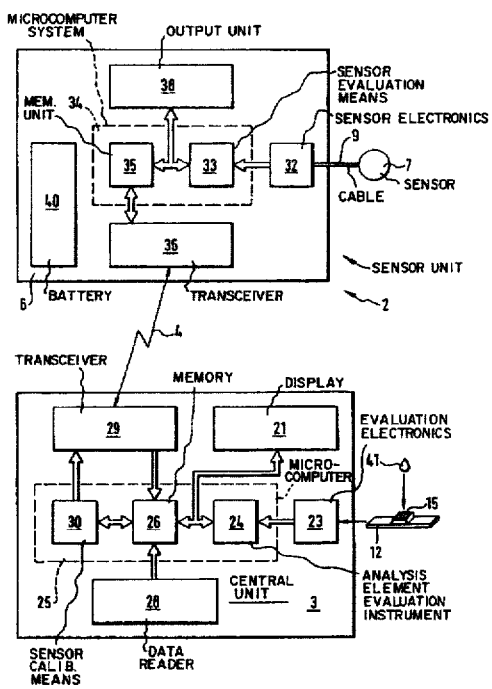

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 5 is cancelled.

Claims 1–4, 6, 7, 15 and 18 are determined to be patentable as amended.

Claims 8–14, 16, 17, 19 and 20, dependent on an amended claim, are determined to be patentable.

New claims 21–26 are added and determined to be patentable.

1. An analytical system for monitoring and analyzing a concentration of a substance in [a] blood [sample] of a patient, said system comprising:
   an element-analysis system, said element-analysis system comprising at least one analysis element containing a reagent thereupon, said reagent for reacting with the substance in *a sample of* the blood when said at least one analysis element has been brought in contact with the sample, thereby causing a measurable change $R$ in the analysis element which correlates with the concentration of the substance[;], *and* an evaluation instrument having a measuring device therein, said measuring device for measuring the measurable change $R$ in the analysis element, the evaluation instrument also including an evaluation means for determining [sample-analysis] *element-analysis* data $C_A$ from the measured change $R$; *said analytical system further comprising*
   *a sensor-analysis, said sensor-analysis system comprising*
   *i)* a [portable] sensor unit *configured to be affixed to and thus continuously carried on the body of the* patient, said [portable] sensor unit including a first sensor means for non-invasive determination of a measured value of a parameter $S$ correlating with the concentration of the substance in the blood of the patient *and for generating sensor data signals representing the non-invasively measured parameter S*, said [portable] sensor unit also including a transmitter means for wireless transmission of data signals representing the non-invasively measured parameter $S$; and
   *ii) an evaluation unit remotely disposed from said sensor unit for wirelessly receiving data signals transmitted from said sensor unit, said evaluation unit comprising receiver means for wirelessly receiving the data signals representing the non-invasively measured parameter S from the sensor unit, and sensor analysis means for ascertaining sensor-analysis data* [from the measured values of the parameter by the first sensor means] $C_S$ *from the transmitted data signals*;
   [said evaluation instrument further comprising a receiver means for wirelessly receiving the data signals from the sensor unit, calibration means for calibrating the sensor-analysis data based upon the sample analysis data, and] *wherein said evaluation unit of the sensor-analysis system and said evaluation instrument of the element-analysis system are coupled together in a central unit which is remote from said sensor unit, said central unit including a calibration means for performing a calibration of the data representing the non-invasively measured parameter S and for determining sensor-analysis data $C_S$ based upon the element-analysis data $C_A$, said central unit also comprising a data memory means coupled to said calibration means for storing data therein.*

2. An analytical system as recited in claim 1, wherein the [portable] sensor unit comprises a light source for irradiating light into living tissue of the patient, and a light detector for detecting light exiting the living tissue of the patient, after the light has interacted with the tissue, thereby providing data indicative of a physical light property which varies based upon an interaction of the light with the tissue, thereby resulting in the parameter $S$ which correlates with the concentration of the analyzed substance in the patient blood, and wherein the sensor analysis data $C_S$ is ascertained from the parameter $S$.

3. An analytical system as recited in claim 1, wherein said [portable] sensor unit comprises a base unit and the first sensor means, said base unit and said first sensor means being operably connected by cables, said base unit including a power supply for the first sensor means.

4. An analytical system as recited in claim 3, wherein the [portable] sensor unit further comprises a second sensor means, said second sensor means being connected by a cable to the base unit, wherein said first and second sensor means provide first and second measured values for correlation with the concentration of the analyzed substance in the patient blood.

6. An analytical system as recited in claim [5] *7*, wherein the [portable] sensor unit also comprises *processing means for processing said sensor data signals and for generating sensor-analysis data $C_S$ therefrom, and* display means for displaying information representing the sensor analysis data.

7. An analytical system as recited in claim [5] *1*, wherein the transmitter means of the [portable] sensor unit and the receiver means of the evaluation instrument are configured to form a transceiver system, said transceiver system conducting an interactive data exchange between the sensor unit and the evaluation instrument.

15. A method for monitoring and analyzing a concentration of a substance in [a] blood [sample] of a patient, comprising the steps of:
   applying [the] *a* blood sample to an analysis element having a reagent thereupon, wherein said reagent reacts with the substance in the blood sample, thereby causing a measurable change $R$ in the analysis element correlating with the concentration of the substance;
   measuring the measurable change $R$ in the analysis element *with an element-analysis system*;
   inputting measurement values of [said] *the* measurable change $R$ into an evaluation instrument *of said element-analysis system* for determining [sample-analysis] *element-analysis* data $C_A$ based upon the measured change $R$;
   non-invasively measuring a parameter $S$ correlating with the concentration of the substance in the blood of the patient with a [portable] sensor unit *of a sensor-analysis system, said sensor unit affixed to a body of the patient and remotely disposed from said evaluation* instrument, said step of non-invasively measuring including the steps of irradiating light into living tissue of the patient, and detecting *a physical property of* light exiting the living tissue[, thereby providing data indicative of a physical light property] which varies based upon an interaction of the light with the tissue, *for generating signals corresponding to the parameter S*;

wirelessly transmitting data signals representing the non-invasively measured value *from the sensor unit via a wireless transmitter* to a receiver *of an evaluation unit* which *is remotely disposed from said sensor unit and* is a part of the [evaluation instrument] *sensor analysis system, and which is coupled in a central unit to said element-analysis system*;

receiving said wirelessly transmitted data signals in the receiver;

determining sensor-analysis data $C_S$ from the transmitted data signals *using a calibration based on a comparison of the transmitted data signals to element-analysis data $C_A$ in said evaluation unit*, said sensor-analysis data $C_S$ representing the concentration of the substance in the blood of the patient.

18. A method for monitoring and analyzing a concentration, of a substance in [a] blood [sample] of a patient, said method comprising the steps of:

providing an evaluation instrument *of an element-analysis system* for evaluating a concentration of a substance in a blood sample[, said step of evaluating comprising the steps of] *of the patient;* providing a sensor-analysis system including a sensor unit configured to be affixed to and continuously carried on the body of the patient, and an evaluation unit remotely disposed from the sensor unit;

applying the blood sample to an analysis element having a reagent thereupon, wherein said reagent reacts with the substance in the blood sample, thereby causing a measurable change $R$ in the analysis element correlating with the concentration of the substance, measuring the mesaurable change $R$ in the analysis element, determining [sample-analysis] *element-analysis* data $C_A$ based upon the measured change $R$, inputting the [sample-analysis] *element-analysis* data $C_A$ to said evaluation [instrument] *unit of said sensor-analysis system*, thereby providing calibration information therefor; said method further comprising the steps of non-invasively measuring a parameter $S$ correlating with the concentration of the substance in the blood of the patient with [a portable] *the* sensor unit *of the sensor-analysis system*, said step of non-invasively measuring including the steps of iradiating light into living tissue of the patient, and detecting *a physical property of* light exiting the living tissue[, thereby providing data indicative of a physical light property] which varies based upon an interaction of the light with the tissue, *for generating signals corresponding to the parameter S*;

wirelessly transmitting data signals representing the non-invasively measured value *from the sensor unit* to a receiver *of the sensor-analysis system, said receiver being remotely disposed from said sensor unit and being coupled to said element-analysis system*;

receiving said wirelessly transmitted data signals in the receiver; *and* determining sensor-analysis data $C_S$ from the transmitted data signals *using a calibration which is based on a comparison of the transmitted data signals to element-analysis data $C_A$ in said evaluation unit*, said sensor-analysis data $C_S$ representing the concentration of the substance in the blood of the patient.

*21. A method as recited in claim 18, wherein said evaluation instrument of said element-analysis system and said receiver of the sensor-analysis system are remotely disposed in a central unit, said receiver being in wireless communication with said sensor unit.*

22. An analytical system as recited in claim 1, wherein said sensor unit is configured to wirelessly transmit said data signals at random operation intervals.

23. A method as recited in claim 15, wherein said step of wirelessly transmitting data signals occurs at random intervals.

24. A method as recited in claim 15, wherein said applying step, measuring step, and inputting steps occur at random intervals.

25. A method as recited in claim 18, wherein said step of wirelessly transmitting data signals occurs at random intervals.

26. A method as recited in claim 18, wherein said applying step, measuring step, and inputting steps occur at random intervals.

* * * * *